United States Patent [19]

Webb

[11] 4,329,292

[45] May 11, 1982

[54] CONTINUOUS METHOD FOR MAKING AROMATIC BIS(ETHER PHTHALIC ACID) OR AROMATIC BIS(ETHER ANHYDRIDE)

[75] Inventor: Jimmy L. Webb, Schenectady, N.Y.

[73] Assignee: General Electric Company, Schenectady, N.Y.

[21] Appl. No.: 254,815

[22] Filed: Apr. 16, 1981

[51] Int. Cl.$^3$ .................... C07C 63/00; C07D 307/89
[52] U.S. Cl. .................................... 549/241; 562/473
[58] Field of Search ..................... 260/346.3; 562/473

[56] References Cited

U.S. PATENT DOCUMENTS

| | | | |
|---|---|---|---|
| 3,879,428 | 4/1975 | Heath et al. | 260/346.3 |
| 3,957,862 | 5/1976 | Heath et al. | 562/473 X |
| 4,116,980 | 9/1978 | Webb | 260/346.3 |
| 4,128,574 | 12/1978 | Markezich et al. | 562/473 |

*Primary Examiner*—Richard Raymond
*Attorney, Agent, or Firm*—Peter A. Bielinski; James C. Davis, Jr.; Joseph T. Cohen

[57] ABSTRACT

A method is provided for continuously converting aromatic bis(ether N-organo substituted phthalimides) to aromatic bis (ether anhydrides) by heating a biphasic aqueous-organic mixture of aromatic bis(ether N-organo substituted phthalimide), phthalic acid and an exchange catalyst in a heated coiled tube reactor to produce an aqueous phase containing aromatic bis (ether phthalic acid) and an organic phase containing N-organo substituted phthalimide which can then be separated and aromatic bis(ether phthalic anhydride) recovered from the aqueous phase.

15 Claims, No Drawings

CONTINUOUS METHOD FOR MAKING AROMATIC BIS(ETHER PHTHALIC ACID) OR AROMATIC BIS(ETHER ANHYDRIDE)

CROSS REFERENCE TO RELATED APPLICATIONS

Reference is made to copending application Ser. No. 251,019 filed Mar. 16, 1981 of Jimmy L. Webb and Donald L. Phipps, for Method of Making Aromatic Bis(Ether Anhydride)s, copending application Ser. No. 250,804, filed Apr. 3, 1981 of Jimmy L. Webb, for Method for Making Aromatic Bis(Ether Anhydride)s, copending application Ser. No. 253,446, filed Apr. 13, 1981 of Jimmy L. Webb and Bharat M. Mehta for Method for Making Aromatic Bis(Ether Anhydride) and application Ser. No. 250,994 filed Apr. 3, 1981 of Jimmy L. Webb, Method for Making Aromatic Bis(Ether Phthalic Acid) or Aromatic Bis(Ether Anhydride) which are assigned to the same assignee as the present invention.

BACKGROUND OF THE INVENTION

Prior to the present invention as shown by Heath, et al. U.S. Pat. Nos. 3,879,428 and 3,957,862, assigned to the same assignee as the present invention, aromatic bis(ether anhydrides) (hereinafter referred to as "bisanhydrides") of the general formula:

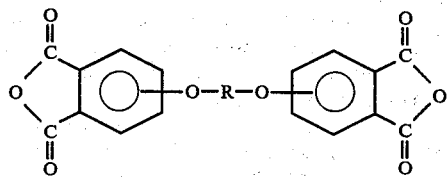

were made by a multi-step procedure involving the base hydrolysis of an aromatic bis(ether N-organo substituted phthalimide) of the formula:

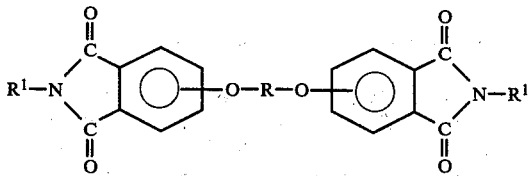

A more specific compound of which is 2,2-bis[4-(3,4-dicarboxy)phenyl]propane bis-N-methylimide which has the formula:

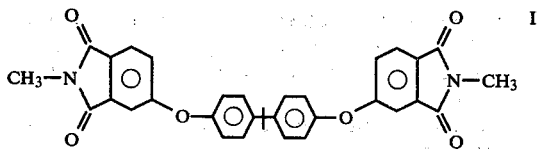

where R is a divalent aromatic radical having from 6–30 carbon atoms and $R^1$ is a monovalent organic radical selected from the class consisting of $C_{(1-8)}$ alkyl radicals, and organic radicals, having from 6–20 carbon atoms, for example, aromatic hydrocarbon radicals and halogenated derivatives thereof. This procedure produced a tetra-acid salt which was thereafter acidified to the tetra-acid followed by the dehydration of the tetra-acid to produce the aromatic bis(ether anhydride) of formula I.

Although the procedure of Heath et al. provides a valuable route to both the aromatic bis(ether phthalic acids) and aromatic bis(ether phthalic anhydrides) it requires the base hydrolysis of the aromatic bis(ether N-organo substituted phthalimide of formula II and the conversion of the resulting salt to the tetra-acid, followed by the dehydration of the tetra-acid. In addition to requiring a variety of steps to convert the bisimide to a bisanhydride, inorganic salts are generated causing disposal problems. Efforts, are, therefore, being directed to providing a more simplified procedure for making the bisanhydride of formula I, or its tetra-acid precursor.

Markezich, et al. U.S. Pat. No. 4,128,574 discloses an imide-anhydride exchange reaction resulting in the production of organic polycarboxylic acids, anhydrides thereof, or organic imides. For example, in particular instances, a bisimide of formula IIA, is heated with phthalic anhydride in the presence of water to effect an exchange between the aforementioned bisimide and the phthalic anhydride to provide the corresponding tetra-acid or anhydride thereof.

Although the Markezich, et al. method eliminates many of the disadvantages of the prior art, such as the formation of inorganic salts or the requirement of a multi-step procedure, Markezich, et al. is essentially a batch method. The recovery of a tetra-acid or bisanhydride at a satisfactory yield, 80% or higher concentration, requires several heating and stripping cycles. It is also difficult to achieve substantial conversion of the bisimide to the tetra-acid or the bisanhydride without resort to the recycling of excessive amounts of phthalic acid or phthalic anhydride. Based on the nature of the exchange between the bisimide and phthalic acid or phthalic anhydride, optimum conversion cannot be realized unless the N-organo phthalimide of the general formula:

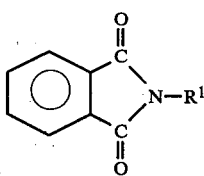

where $R^1$ is as previously defined, which is also formed in the reaction, is separated from the mixture.

Webb, in U.S. Pat. No. 4,116,980, showed that optimum conversion of the bisimide to the tetra-acid or dianhydride thereof, can be achieved based on the imide-anhydride exchange in the presence of water, as shown by the following:

where A and A' are imides and B and B' are anhydrides, if the A' imide is selectively removed from the reaction during the exchange. For example, in the above equation, A can be a bisimide, B can be a phthalic acid, B' can be a bis-anhydride or tetra-acid and A' can be an organo phthalimide. Webb achieved these results by venting a portion of the vapor phase of the reaction mixture consisting of a liquid phase and a vapor phase during the exchange. The vapor phase consisted essentially of water and N-organo phthalimides with very little phthalic acid so that by continuously venting the vapor phase during the exchange, the reaction is driven to the right. It is, therefore, possible to convert the starting bisimide to the corresponding tetra-acid or bis anhydride without either shutting down the reactor or recycling excessive amounts of phthalic acid.

DETAILED DESCRIPTION OF THE INVENTION

The present invention is based on the development of a continuous biphasic imide anhydride exchange process in which an inert organic solvent solution of an aromatic bis(ether N-organo substituted phthalimide) hereinafter also identified as "BI" is contacted with an aqueous solution of phthalic acid hereinafter also identified as "PA" and an exchange catalyst at an elevated temperature in a heated coiled tube reactor. Imide-anhydride exchange occurs and a major portion of the bis-compound moves from the organic phase to the aqueous phase where it exists as the salt of the aromatic bis(ether phthalic acid) hereinafter also identified as "TA" of the general formula:

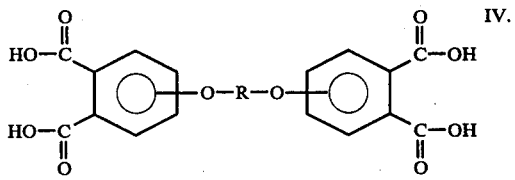

where R is as previously defined. This compound is easily converted by dehydration to the aromatic bis(ether phthalic anhydride) hereinafter also identified as "DA" of formula I. The N-organo phthalimide hereinafter also identified as "PI" formed by the exchange moves out of the aqueous phase and into the organic phase thereby facilitating an increased conversion of the BI to the TA. Unreacted (excess) phthalic acid remains in the aqueous phase as a salt.

Before the exchange reaction, all imides (PI and BI) exist in the organic phase and all acids and catalysts exist in the aqueous phase. After the exchange reaction, when equilibration is established, the major portion of the BI has moved from the organic phase to the aqueous phase where it exists as a salt of the TA. The phthalic imide, hereinafter also identified as "PI", formed by the exchange moves into the organic phase along with the unreacted BI and some aromatic bis(ether N-organo substituted phthalimide ether anhydride) hereinafter identified as "IA" of the general formula:

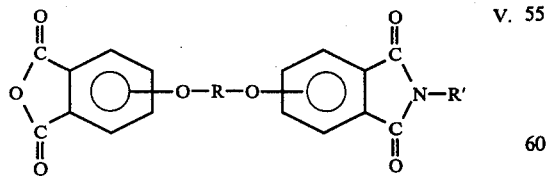

where R and R' are as previously defined. Therefore, at equilibrium except for a small amount of IA present in both phases, the original condition, with all imides being present in the organic phase and all acids or salts of the acids being present in the aqueous phase, still exists.

Corrosion problems associated with previous methods can be substantially eliminated by neutralization of all acids by using an amine catalyst at a mole ratio of at least 2:1 with respect to PA, and in addition the biphasic exchange process makes possible a clean separation of the N-organo phthalimide from the phthalic acid. The exchange can also be rapidly catalyzed, requires substantially less process energy than the previous methods and conserves reactants, solvents and catalyst.

The elevated temperature and pressure requirements for the imide-anhydride exchange reaction are easily accommodated in the laboratory by simple autoclaves. However, on an industrial scale such heavy walled pressure equipment becomes very expensive. In addition, agitation of the contents of the autoclaves which would facilitate shorter reaction times becomes very difficult since this type of equipment with moving parts and high pressure seals around rotating shafts is very expensive and difficult to maintain. Mixing is a prime concern in attaining equilibrium with the biphasic system of the present invention. Mixing can be obtained by passing the biphasic mixture through a coil of tubing held in a horizontal position. Due to density differences the organic phase rises through the aqueous phase on the ascending side of the coil and the aqueous phase falls through the organic phase on the descending side of the coil. The process continues along the length of the coil and gives good contact between the two phases and consequently accelerates the equilibration process.

There is provided by the invention a continuous biphasic imide-anhydride exchange process for making aromatic bis(ether phthalic acid) from aromatic bis(ether phthalimide) which comprises, (A) passing through a heated coiled tube reactor at an elevated temperature, e.g., from 170°–260° C., and under superatmospheric pressure, e.g., from between 200–700 psi, a mixture comprising:
 (i) aromatic bis(ether phthalimide) of formula II
 (ii) 2–20 moles of phthalic anhydride or phthalic acid per mole of (i),
 (iii) a sufficient and effective amount of an exchange catalyst,
 (iv) 0.01–100 parts of water per part, by weight, of (i),
 (v) 0.01–100 parts of a water-immiscible inert organic solvent per part, by weight, of (i), to produce an equilibrated liquid biphasic reaction mixture, comprising an aqueous phase having selectively dissolved therein, the aromatic bis(ether phthalic acid) formed in the exchange reaction, the exchange catalyst together with any unreacted phthalic acid, and an organic phase having selectively dissolved therein, N-organo substituted phthalimide of formula III which was also formed in the exchange reaction, together with any unreacted aromatic bis(ether phthalimide), (B) separating the organic phase from the aqueous phase, and (C) recovering the aromatic bis(ether phthalic acid) from the aqueous phase.

Radicals included by R are for instance,

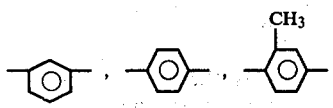

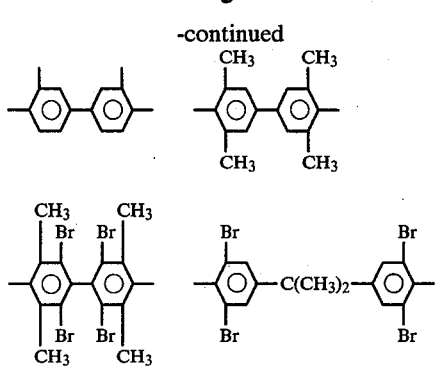

and divalent organic radicals of the general formula:

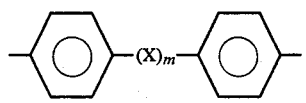

where X is a member selected from the class consisting of divalent radicals of the formulas, $-C_yH_{2y}-$,

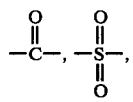

$-O-$, $-S-$, where m is 0 or 1, and y is a whole number from 1 to 5 inclusive.

Radicals included by $R^1$ are for example, phenyl tolyl, xylyl, napthyl, chlorophenol, bromonaphthyl, etc. and alkyl radicals, such as methyl, ethyl, propyl, etc.

The bisimides of formula II and a method for making them, are more particularly described in the aforementioned U.S. Pat. No. 3,879,428, Wirth et al., which is based on the initial formation of N-organo substituted phthalimide of the formula:

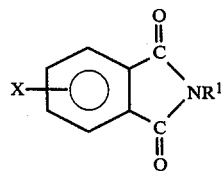

VI.

where X is a redical selected from the class consisting of nitro, halo, e.g. chloro, fluoro, bromo, etc., and $R^1$ is as previously defined. The phthalimide of formula VI can be formed by effecting a reaction between X-substituted phthalic anhydride and an organic amine, such as aniline, toluidine, methyl amine, ethyl amine, etc.

Included by the phthalimides of formula VI are, for example, N-methyl-4-nitrophthalimide, N-phenyl-3-nitrophthalimide, N-phenyl-4-nitrophthalimide, N-methyl-3-nitrophthalimide, N-butyl-4-nitrophthalimide, etc. As further shown in U.S. Pat. No. 3,879,428, the aromatic bis(ether phthalimide)s of formula II can be made by effecting reaction between phthalimides of formula VI and an alkali diphenoxide of the general formula:

VII. $M-O-R-O-M$ where R is as previously defined, and M is a metal ion of an alkali metal for example, sodium, potassium, lithium, etc.

Included by the alkali diphenoxides of formula VII, are sodium and potassium salts of the following dihydric phenols.

2,2-bis(2-hydroxyphenyl)propane;
2,4'-dihydroxydiphenylmethane;
bis-(2-hydroxyphenyl)methane;
2,2-bis-(4-hydroxyphenyl)propane hereinafter identified as "Bisphenol-A" or "BPA",
1,1-bis-(4-hydroxyphenyl)ethane;
1,1-bis-(4-hydroxyphenyl)propane;
2,2-bis-(4-hydroxyphenyl)pentane;
3,3-bis-(4-hydroxyphenyl)pentane;
4,4'-dihydroxybiphenyl;
4,4'-dihydroxy-3,3,5,5'-tetramethylbiphenyl;
2,4'-dihydroxybenzophenone;
4,4'-dihydroxydiphenylsulfone;
2,4'-dihydroxydiphenylsulfone;
4,4'-dihydroxydiphenyl sulfoxide,
2,4'-dihydroxydiphenyl sulfoxide;
4,4'-dihydroxydiphenyl sulfide;
hydroquinone;
resorcinol;
3,4'-dihydroxydiphenylmethane;
4,4'-dihydroxybenzophenone;
4,4'-dihydroxydiphenylether, etc.

Exchange catalysts which can be employed in the invention are; acids such as sulfuric, phosphoric, hydrochloric, methanesulfonic, fluoroboric, toluenesulfonic, acetic, butyric, trifluoroacetic acids, etc.; metal salts, such as $FeCl_3$, $ZnCl_2$, $SnCl_4$, $AlCl_3$, and their bromides; trialkyl amines hereinafter also identified as "$R_3N$", such as trimethylamine, triethylamine, tripropylamine, tributylamine, etc. with preferred catalysts being triethylamine and trimethylamine.

Organic solvents which can be used in the invention are inert, water immiscible solvents which selectively dissolve any imide compounds present initially or formed during the exchange reaction for example, toluene, benzene, xylene, chlorobenzene and orthodichlorobenzene.

The coiled tube reactor of the present invention may be constructed of any tubing which will withstand the temperatures and pressure of the reaction and will not be attacked by the biphasic process reaction mixture. Examples of tubing which can be used are 316 stainless steel, 347 stainless steel, glass, etc.

The length of the tubing (1), cross sectional area of the tubing (a), and flow rate (r), effect the rate of the exchange reaction and consequently the residence time (t) required to approach equilibration. These parameters are related by $1a/r=t$. Kenetic studies indicated that a residence time of $\sim 2$ hours was needed.

The coiled tube reactor is heated, for example, by an oil filled heating jacket or other conventional means.

The following broad and preferred parameters have been determined for the bi-phasic imide-anhydride continuous hot tube reactor process:

| 1. | Temperature | Range 170°–260° |
| | | Preferred 185–225° C. |
| 2. | Pressure | Determined by temperature |
| | | Range 200–700 psi |
| 3. | PA to BI Mole Ratio | Range 2:1 to 20:1 |
| | | Preferred 4–6:1 |
| 4. | Catalyst to PA Mole | Range 1:1 to 3:1 |

-continued

| | Ratio | Preferred ~2:1 |
|---|---|---|
| 5. | Organic solvent to water weight ratio | Range 0:1 to 10:1 Preferred ~4:1 |
| 6. | Solids Content | Range 1% to 60% Preferred ~10-15% |
| 7. | PA Concentration in aqueous phase | Range 0.2-6 mole/liter Preferred ~3 mole/liter |
| 8. | BI Concentration in Organic Phase | Range 0.02-1 mole/liter Preferred ~0.2 mole/liter |

In the practice of the invention an aqueous solution containing PA and an exchange catalyst and an organic solution containing the BI are combined and fed into the coiled tube reactor under pressure. Heating of both reactant phases is generally required to maintain higher concentration reactant solutions. After passage through the reactor the phases are separated by conventional means and the solvents, reactants and catalysts are distilled off for optional recycling. The PI recovered from the organic phase can be nitrated and used to produce more BI. The TA product in the aqueous phase yields the DA product after dehydration.

EXAMPLE I

The hot tube reactor was 24 feet of 10.9 mm I.D. 347 stainless steel tubing with a volume of 640 cc, formed into a multiturn 16 cm diameter coil oriented in a horizontal position with respect to the coil axis. The reactor coil was enclosed in a copper jacket and heated to 200° C. with flowing hot oil. The pressure in the reactor was maintained at 500 psi to prevent boiling of the contents.

An aqueous solution of 2.98 mole/liter PA and 4.5 mole/liter triethylamine catalyst was heated to 65° C. to prevent crystallization and pumped to the coiled hot tube reactor at a rate of 3 ml/min.

A toluene solution of 0.22 mole liter BI was heated to 80° C. and pumped to the hot tube reactor at 7 ml/min. These flow rates result in a PA to BI mole ratio of 5.75:1.

The total running time was ~6 hrs. with a total flow rate of 10 ml/min and samples were taken every 6 minutes after the calculated residence time.

The reactor was initially filled with aqueous PA solution.

The samples of both phases were stirred of solvent under vacuum (~25 mm) and 200° C., and analyzed by liquid chromatography (Waters Associates LC, corisol-I column ⅛"×2', solvent=40% $CH_2Cl_2$, 59.5% $CHCl_3$ and 0.5% $Et_2O$; flow rate=2 ml/min, detector=UV, 254).

The results are given below in Table 1, where the concentration of bis-compounds (BI+IA+TA) is given in grams per liter and the concentration of TA in the bis-compounds is given in mole %.

The data shows a steady state or equilibrium was reached at ~120 min. and thereafter no additional mass was transferred from the organic phase and the mole % TA remained unchanged at ~75%.

TABLE 1

Composition of the Imide-Anhydride Exchange Product From The Coiled Hot Tube Reactor

| Time (Minutes) | bis-compounds* g/liter | Mole % TA in bis-compounds |
|---|---|---|
| 39 | 8.99 | 43 |
| 50 | 33.33 | 70 |
| 60 | 87.66 | 83 |
| 72 | 119.33 | 81 |

TABLE 1-continued

Composition of the Imide-Anhydride Exchange Product From The Coiled Hot Tube Reactor

| Time (Minutes) | bis-compounds* g/liter | Mole % TA in bis-compounds |
|---|---|---|
| 81 | 146.33 | 79 |
| 93 | 163.33 | 76 |
| 105 | 170.66 | 75 |
| 120 | 182.00 | 75 |
| 135 | 184.03 | 77 |
| 152 | 186.60 | 74 |
| 170 | 188.00 | 74 |
| 189 | 186.66 | 74 |
| 205 | 183.30 | 75 |

*bis-compounds = BI + IA + TA

The above results show that a continuous biphasic exchange reaction carried out in a coiled hot tube reactor is capable of providing a product having at least ~75 mole percent TA after one pass through the reactor. The product from the first pass was sent back through the reactor under the same conditions except the toluene contained no BI. This resulted in a product having ~95 mole % TA. A third pass, again with toluene only in the organic phase, gives a product with at least 97 mole % TA.

EXAMPLE-II

The initial conditions and concentrations were the same as in Example-I, however, the flow rate for the aqueous phase and the organic phase were both 5 ml/min. This results in a PA to BI mole rate of 13.42:1.

The results are given below in Table-II.

TABLE 2

Coiled Hot Tube Reactor Product Composition

| Time (min.) | bis-compound Concentration g/liter | mole % TA in bis-compounds |
|---|---|---|
| 56 | 67.6 | 88 |
| 68 | 94.9 | 88 |
| 81 | 100.0 | 88 |
| 93 | 102.0 | 88 |
| 105 | 104.0 | 88 |
| 116 | 100.6 | 88 |
| 128 | 100.3 | 88 |
| 141 | 101.1 | 88 |

These data show that a steady state is established after ~81 min. and yields a product having ~88 mole % TA. The shorter time to reach equilibrium, 81 min. vs. 120 min. in Example 1, and a higher mole % TA, 88% vs. 77% in Example 1, are due to higher PA to BI mole ratio, 13.42:1 vs. 5.75:1 in Example I.

Other modifications and variations of the present invention are possible in the light of the above teachings. It is, therefore, to be understood that changes may be made in the particular embodiments described above which are within the full intended scope of the invention as defined in the appended claims.

What is claimed is:

1. A continuous biphasic imide-anhydride exchange process for making aromatic bis(ether phthalic acid) of the formula:

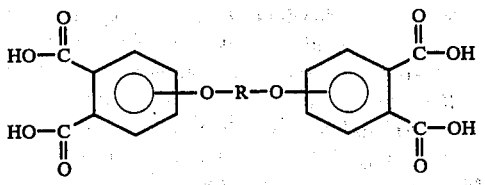

or the anhydride thereof which comprises:
(A) passing a mixture comprising:
(i) aromatic bis(ether phthalimide of the formula:

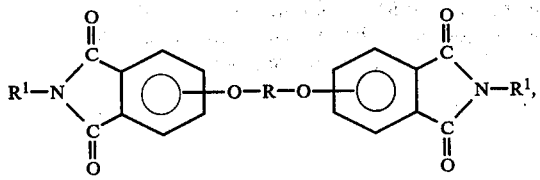

(ii) phthalic anhydride or phthalic acid
(iii) an exchange catalyst
(iv) water
(v) a water-immiscible inert organic solvent through a heated coiled tube reactor to produce an equilibrated liquid biphasic reaction mixture comprising an aqueous phase having selectively dissolved therein the aromatic bis(ether phthalic acid) formed in the exchange reaction, the catalyst, along with any excess phthalic acid, and an organic phase having selectively dissolved therein, N-organo substituted phthalimide of the formula:

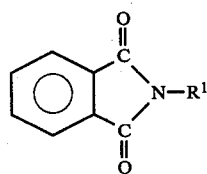

which was also formed in the exchange reaction, together with any unreacted aromatic bis(ether phthalimide),
(B) separating the organic phase from the aqueous phase
(C) recovering the aromatic bis(ether phthalic acid) from the aqueous phase, and optionally dehydrating it to form the dianhydride, where R is a divalent aromatic radical having from 6-30 carbon atoms and $R^1$ is a monovalent organo radical selected from the class consisting of $C_{(1-8)}$ alkyl radicals, and organic radicals having from 6-20 carbon atoms selected from the class consisting of aromatic hydrocarbon radicals and halogenated derivatives thereof.

2. The process of claim 1 wherein the reaction temperature is between about 170° C.-260° C. and the reaction pressure is between about 200 psi-700 psi.

3. The process of claim 1 wherein the phthalic acid or anhydride is present at an amount of between about 2-20 moles per mole of aromatic bis(etherphthalimide).

4. The process of claim 1 wherein the exchange catalyst is a trialkyl amine.

5. The process of claim 4 wherein the exchange catalyst is triethyl amine.

6. The process of claim 1 wherein the catalyst is present in a mole ratio of from about 1 to 3 moles of catalyst per mole bis(imide).

7. The process of claim 1 wherein, on a weight basis, the amount of water used is between about 0.01 and 100 parts of the latter per part bis(imide).

8. The process of claim 1 wherein the organic solvent is toluene.

9. The process of claim 1 wherein, on a weight basis, the amount of solvent used is between 0.01 and 100 parts of the latter per part bis(imide).

10. The process of claim 1 wherein $R^1$ is methyl.

11. The process of claim 1 wherein the aromatic bis(ether phthalic acid) is 2,2-bis[4-(3,4-dicarboxyphenoxy)phenyl]propane.

12. The process of claim 1 wherein the bis(ether N-organo substituted phthalimide) is 2,2-bis[4-(3,4-dicarboxyphenoxy)phenyl]propane bis-N-methylimide.

13. A continuous biphasic imide-anhydride exchange process for making aromatic bis(ether phthalic acid) of the formula:

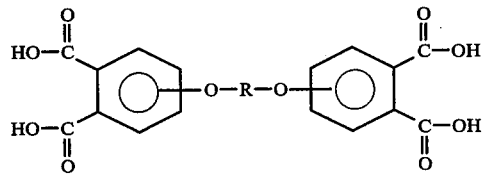

or the anhydride thereof from aromatic bis(ether phthalimide) which comprises:
(A) heating at a temperature of 170°-260° C. and a pressure of 200-700 psi, a mixture comprising:
(i) aromatic bis(ether phthalimide) of the formula:

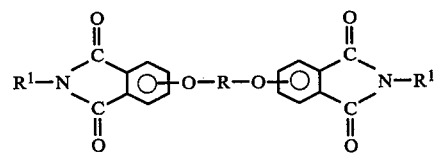

(ii) 2-20 moles phthalic anhydride or phthalic acid per mole of (i).
(iii) 1-3 moles of a trialkylamine exchange catalyst per mole of (i).
(iv) 0.01-100 parts of water per part by weight of (i).
(v) 0.01-100 parts of a water immiscible organic solvent per part by weight of (i) through a coiled tube reactor at 170° C.-260° C. and a pressure of 200-700 psi to produce an equilibrated liquid biphasic reaction mixture, comprising an aqueous phase having selectively dissolved therein the aromatic bis(ether phthalic acid) formed in the exchange reaction, the trialkylamine catalyst, along with any excess phthalic acid, and an organic phase having selectively dissolved therein, N-organo substituted phthalimide of the formula:

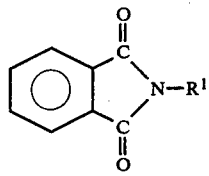

which was also formed in the exchange reaction, together with any unreacted aromatic bis(ether phthalimide),
(B) separating the organic phase from the aqueous phase
(C) recovering the aromatic bis(ether phthalic acid) from the aqueous phase, where R is a divalent aromatic radical having from 6–30 carbon atoms, $R^1$ is a monovalent organo radical selected from the class consisting of $C_{(1-8)}$ alkyl radicals, and organic radicals having from 6–20 carbon atoms selected from the class consisting of aromatic hydrocarbon radicals and halogenated derivatives thereof and X is a radical selected from the class consisting of the nitro group and halogen.

14. The biphasic amide-anhydride exchange process of claim 1 wherein the sequence, reaction step A-separation step B, is repeated at least once before the recovery step C.

15. The process of claim 14 wherein the unreacted aromatic bis(ether phthalimide), unreacted phthalic anhydride or phthalic acid, catalysts and solvents are recycled in a continuous manner.

* * * * *